(12) United States Patent
Raman et al.

(10) Patent No.: US 9,721,061 B2
(45) Date of Patent: Aug. 1, 2017

(54) DE NOVO DESIGN OF ALLOSTERIC PROTEINS

(71) Applicant: President and Fellows of Harvard College, Cambridge, MA (US)

(72) Inventors: Srivatsan Raman, Arlington, MA (US); Noah D. Taylor, Boston, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/120,228

(22) PCT Filed: Feb. 20, 2015

(86) PCT No.: PCT/US2015/016868
§ 371 (c)(1),
(2) Date: Aug. 19, 2016

(87) PCT Pub. No.: WO2015/127242
PCT Pub. Date: Aug. 27, 2015

(65) Prior Publication Data
US 2017/0132358 A1  May 11, 2017

Related U.S. Application Data

(60) Provisional application No. 61/942,755, filed on Feb. 21, 2014.

(51) Int. Cl.
*G06F 19/16* (2011.01)
*G01N 33/53* (2006.01)
*C07K 14/00* (2006.01)

(52) U.S. Cl.
CPC ............. *G06F 19/16* (2013.01); *C07K 14/00* (2013.01); *G01N 33/5308* (2013.01)

(58) Field of Classification Search
None
See application file for complete search history.

(56) References Cited

U.S. PATENT DOCUMENTS

| 7,476,500 B1 | 1/2009 | Liu et al. |
| 2009/0263851 A1 | 10/2009 | Liu et al. |
| 2011/0287485 A1 | 11/2011 | Bowers et al. |

FOREIGN PATENT DOCUMENTS

| WO | 02074978 A2 | 9/2002 |
| WO | 2008103475 A1 | 8/2008 |

OTHER PUBLICATIONS

International Search Report re corresponding PCT/US2015/016868 dated Jul. 8, 2015.
Glass, Christopher K., et al, The coregulator exchange in transcriiptional functions of nuclear receptors, Genes Dev., Jan. 15, 2000, vol. 14, No. 2, pp. 121-141.
Laskowski, Roman A, et al, The structural basis of allosteric regulation in proteins, FEBS Letters, Jun. 5, 2009, vol. 583, No. 11, pp. 1692-1698.
Strickland, Devin et al, Light-activated DNA binding in a designed allosteric protein, Proc Natl Acad Sci USA, Aug. 5, 2008, vol. 105, No. 31, pp. 10709-10714.

*Primary Examiner* — Christopher M Gross
(74) *Attorney, Agent, or Firm* — Banner & Witcoff, Ltd.

(57) ABSTRACT

Methods and compositions for making and isolating allosteric DNA binding proteins that bind to one or more allosteric effectors to induce a conformation change in the proteins are provided.

31 Claims, 2 Drawing Sheets

US 9,721,061 B2

DE NOVO DESIGN OF ALLOSTERIC PROTEINS

RELATED APPLICATIONS

This application is a National Stage Application under 35 U.S.C. 371 of co-pending PCT application PCT/US15/16868 designating the United States and filed Feb. 20, 2015; which claims the benefit of U.S. provisional application No. 61/942,755 and filed Feb. 21, 2014 each of which are hereby incorporated by reference in their entireties.

STATEMENT OF GOVERNMENT INTERESTS

This invention was made with government support under DE-FG02-02ER63445 awarded by the U.S. Department of Energy. The government has certain rights in this invention.

FIELD

The present invention relates to methods and compositions for designing novel allosteric proteins.

BACKGROUND

In rational protein design, detailed knowledge of structure and function of a protein of interest is used to engineer a mutant form of the protein. However, rational mutagenesis methods are generally unsuccessful due to the fact that complex, non-intuitive interactions often govern protein structure and function. Accordingly, it is desirable to develop novel methods and compositions for protein engineering.

SUMMARY

Embodiments of the present invention are based on novel methods and compositions for designing allosteric proteins that respond to a target small molecule or allosteric effector by binding to the target small molecule or allosteric effector and undergoing a subsequent conformational change. In certain aspects of the invention, the methods and compositions described herein can be used to design sensor proteins useful for engineering biosynthetic pathways that are useful e.g., for fermentation-based molecule production. In other aspects of the invention, the methods and compositions described herein can be used to design orthogonal, inducible gene expression systems for use in mammalian cell culture, which is a significant advance over methods such as the Tet-On system presently used by those skilled in the art. In still other aspects of the invention, the methods and compositions described herein can also be used to design inducible gene expression systems useful e.g., for large scale fermentation, which is a significant advance over methods such as the IPTG-based systems presently used by those skilled in the art.

In certain exemplary embodiments, a method of making and isolating allosteric DNA binding proteins that bind to a companion allosteric effector that induces a conformation change in the allosteric DNA binding proteins is provided.

As used herein, the term "allosteric protein" refers to a protein that binds an effector molecule and undergoes a conformational change, causing an increase or a decrease in one or more activities of the protein. An allosteric protein of the present invention can be a sensor and/or part of an inducible gene expression system (e.g., an orthogonal gene expression system). (See Liang et al. (2013) *Biotech. and Bioeng.* 110:1419 for a review.) Allosteric proteins are well-known to those of skill in the art and include transcription factors, riboswitches, two-component signaling proteins, nuclear hormone receptors and the like.

As used herein, an "effector molecule" refers to a molecule, e.g., a small molecule, that selectively binds to an allosteric protein and regulates its biological activity. In this manner, effector molecules act as ligands to increase or decrease one or more of activities including, but not limited to, enzymatic activity, gene expression, cell signalling and the like. In certain aspects, an effector molecule increases the activity of an allosteric protein, i.e., the effector molecule functions as an "allosteric activator." In other aspects, an effector molecule decreases the activity of an allosteric protein, i.e., the effector molecule functions as an "allosteric inhibitor."

In certain exemplary embodiments, candidate allosteric DNA binding proteins having a binding pocket for a desired companion allosteric effector are computationally designed in silico. Nucleic acid sequences encoding the candidate allosteric DNA binding proteins are provided, and subsequently introduced into bacterial host cells and expressing the candidate allosteric DNA binding proteins.

In certain exemplary embodiments, it is determined whether the candidate allosteric DNA binding proteins bind to DNA and inhibit expression of a gene by using negative selection to identify a first plurality of microorganisms (e.g., bacterial host cells (e.g., *Escherichia coli* or *Bacillus subtilis*)) where the candidate allosteric DNA binding proteins have bound to DNA and inhibit expression of the gene. If the DNA binding proteins bind to DNA and inhibit expression of a gene, the microorganisms (e.g., bacterial host cells) will survive. Candidate allosteric DNA binding proteins that do not bind to DNA activate the expression of the gene causing bacterial host cells carrying that allosteric DNA binding protein to die.

In certain exemplary embodiments, it is determined whether the candidate allosteric DNA binding proteins in the first plurality of bacterial host cells bind to the desired companion allosteric effector using positive selection to identify a second plurality of bacterial host cells where the candidate allosteric DNA binding proteins have bound to the companion allosteric effector. Pooled candidate DNA binding proteins from the first plurality of bacterial host cells will be assayed for activation by the desired allosteric effector molecule by positive selection. In positive selection, only the bacterial host cells that carry candidate DNA binding proteins that respond to the desired allosteric effector molecule will survive.

The genome of the microorganism is optionally genetically modified to include DNA encoding for an antidote to a toxin. When expressed, the allosteric protein regulates the production of the antidote within the microorganism. Depending on the nature of the allosteric protein, it can regulate antidote production by repressing in the absence of the allosteric effector, activating in the presence of the allosteric effector, occluding ribosome binding site in the absence of allosteric effector, etc. If the microorganism is placed into an environment of the toxin and no antidote or insufficient antidote is produced, the microorganism will die. The desired allosteric effector can be provided exogenously.

The microorganism is optionally placed into an environment of a toxin counterpart to the antidote. In this manner, the antidote is referred to herein as a "selector" to the extent that antidote is produced by the cell in response to the level of allosteric effector present and in an amount sufficient to prevent the cell from dying. The level of antidote, which is proportional to the level of allosteric effector, selects strains containing candidate allosteric DNA binding proteins for further modification and optimization.

In certain aspects of the invention, negative selection includes contacting the bacterial host cells with a toxin that is toxic to cells which express the gene.

In other aspects of the invention, negative selection includes contacting the bacterial host cells with a toxin that is toxic to cells where the candidate allosteric DNA binding proteins have not bound to DNA to inhibit expression of the gene.

In certain aspects of the invention, positive selection includes contacting the first plurality of bacterial host cells with a toxin and the companion allosteric effector, wherein the toxin is toxic to cells where the gene is not expressed.

In certain aspects of the invention, positive selection includes contacting the first plurality of bacterial host cells with a toxin and allosteric effector targets, wherein the toxin is toxic to cells where the companion allosteric effector has not bound to the candidate allosteric DNA binding proteins in a manner to release the candidate allosteric DNA binding proteins from the DNA.

In certain aspects of the invention, positive selection includes detecting a detectable marker that is expressed in the first plurality of bacterial cells when the candidate allosteric DNA binding proteins have bound to the DNA to express the gene.

In certain aspects of the invention, the detectable marker is a fluorescent protein (e.g., green fluorescent protein (GFP)) that can be detected, e.g., by fluorescence activated cell sorting.

In certain aspects of the invention, the allosteric DNA binding protein regulates the expression of a fluorescent reporter (such as GFP), such that the fluorescent reporter is expressed when the allosteric DNA binding protein is activated by the allosteric effector molecule.

In certain aspects of the invention, the first plurality of cells following negative selection is subjected to an additional screen via fluorescence activated cell sorting (FACS). In certain aspects of the invention, positive screening comprises evaluating the activation of candidate allosteric DNA binding proteins towards the desired allosteric effector wherein only those candidate allosteric DNA binding proteins that report activation by expressing the fluorescent reporter are sorted and collected via FACS.

In certain aspects of the invention, the positive selection further comprises detecting a detectable marker that is expressed in the first plurality of bacterial cells when the companion allosteric effector has not bound to the candidate allosteric DNA binding proteins in a manner to release the candidate allosteric DNA binding proteins from the DNA.

In certain exemplary embodiments, a method of making and isolating allosteric DNA binding proteins that bind to a companion allosteric effector that induces a conformation change in the allosteric DNA binding proteins is provided. The method includes computationally designing in silico candidate allosteric DNA binding proteins having a binding pocket for a companion allosteric effector and providing nucleic acid sequences encoding the candidate allosteric DNA binding proteins. The method further includes introducing the nucleic acid sequences into Escherichia coli host cells and expressing the candidate allosteric DNA binding proteins.

The method includes determining whether the candidate allosteric DNA binding proteins bind to DNA and inhibit expression of a gene by using negative selection to identify a first plurality of Escherichia coli host cells where the candidate allosteric DNA binding proteins have bound to DNA and inhibit expression of the gene.

The method also includes determining whether the candidate allosteric DNA binding proteins in the first plurality of Escherichia coli host cells bind to the companion allosteric effector using positive selection to identify a second plurality of Escherichia coli host cells where the candidate allosteric DNA binding proteins have bound to the companion allosteric effector.

In certain aspects of the invention, the nucleic acid sequences encoding the candidate allosteric DNA binding proteins are created from nucleic acid subsequences bound to a substrate, and are ligated to form the nucleic acid sequences encoding the candidate allosteric DNA binding proteins.

In other aspects of the invention, negative selection includes contacting the bacterial host cells with a toxin that is toxic to cells which express the gene and/or positive selection includes contacting the first plurality of bacterial host cells with a toxin and the companion allosteric effector, wherein the toxin is toxic to cells where the gene is not expressed.

In certain exemplary embodiments, a method of making and isolating allosteric DNA binding proteins that bind to a companion allosteric effector that induces a conformation change in the allosteric DNA binding proteins is provided. The method includes computationally designing in silico candidate allosteric DNA binding proteins having a binding pocket for a companion allosteric effector, providing nucleic acid sequences encoding the candidate allosteric DNA binding proteins created from nucleic acid subsequences bound to a substrate, and introducing the nucleic acid sequences into microorganisms and expressing the candidate allosteric DNA binding proteins.

The method also includes determining whether the candidate allosteric DNA binding proteins bind to DNA and inhibit expression of a gene by using negative selection to identify a first plurality of microorganisms where the candidate allosteric DNA binding proteins have bound to DNA and inhibit expression of the gene.

The method further includes determining whether the candidate allosteric DNA binding proteins in the first plurality of microorganisms bind to the companion allosteric effector using positive selection to identify a second plurality of microorganisms where the candidate allosteric DNA binding proteins have bound to the companion allosteric effector.

In certain aspects of the invention, the substrate is a microarray. In other aspects of the invention, a plurality of subsequences from the substrate are amplified from sequences on the microarray and combined to form the nucleic acid sequences encoding the candidate allosteric DNA binding proteins.

In certain aspects of the invention, the nucleic acid sequences encoding the candidate allosteric DNA binding proteins are generated randomly (e.g. by error-prone PCR or combinatorial PCR).

In certain aspects of the invention, the candidate allosteric DNA binding proteins are fused to an anti-toxin gene requiring the protein reading frame to remain intact for its function. Candidate allosteric DNA binding proteins in which the reading frame is not intact do not allow expression of the anti-toxin protein, and the host cells carrying them may be eliminated by exposing the cells to the toxin.

BRIEF DESCRIPTION OF THE DRAWINGS

The patent or application file contains drawings executed in color. Copies of this patent or patent application publication with the color drawings will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION OF CERTAIN EMBODIMENTS

Figure 1:
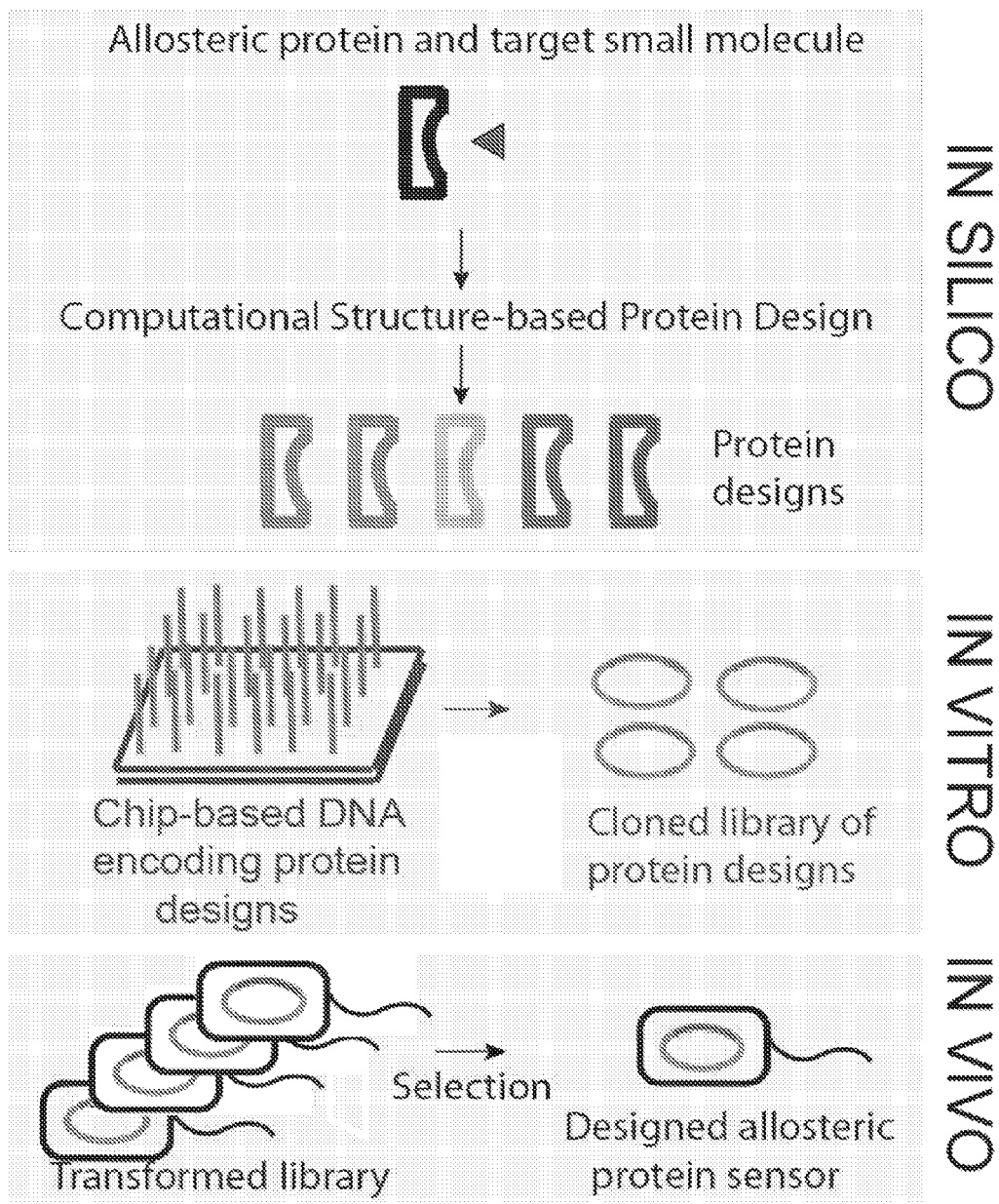
FIG. 1 schematically depicts a method according to exemplary embodiments of the present invention for the de novo design of allosteric proteins. The method combines in silico, in vitro and in vivo steps to engineer novel allosteric proteins that exhibit high binding affinity and allostery.
Figure 2:
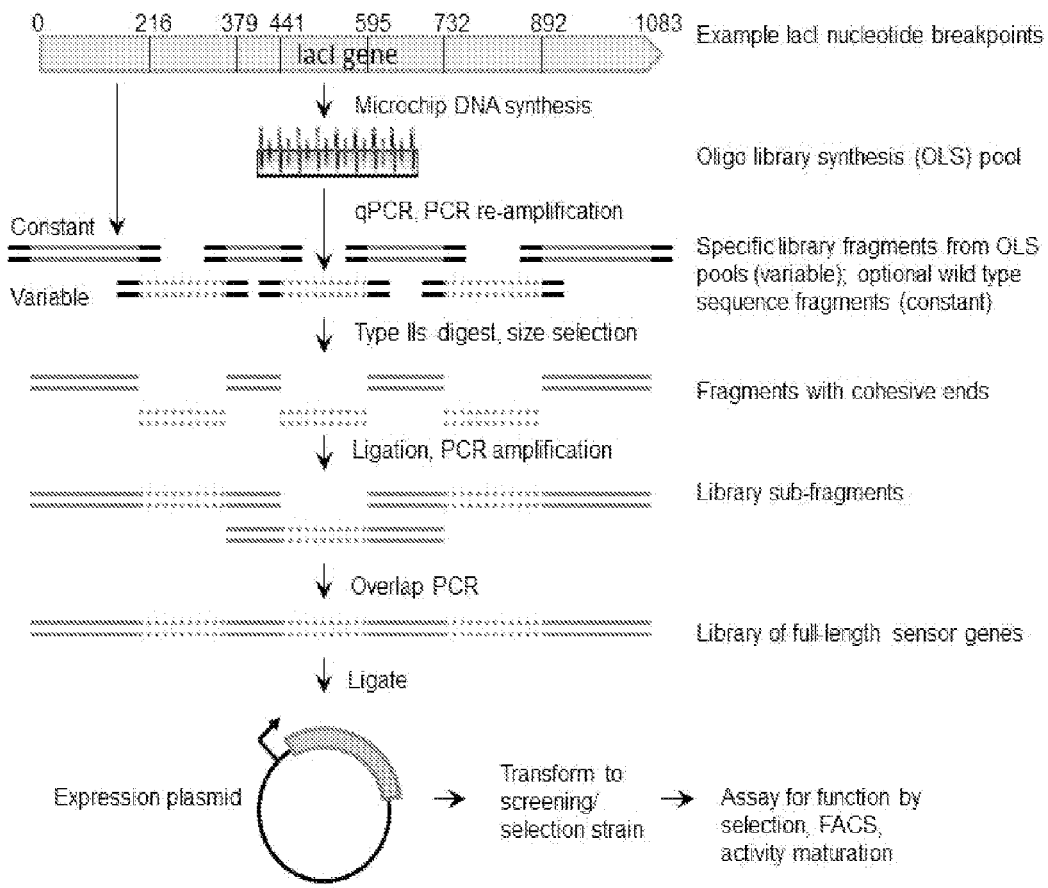
FIG. 2 schematically depicts a sensor redesign library construction method according to certain embodiments of the invention.

Embodiments of the present invention provide novel methods and compositions for protein engineering. In certain exemplary embodiments, one method of the invention combines the steps of computationally designing candidate protein sequences, synthesizing nucleic acid sequences encoding the candidate protein sequences, and using a selection system whereby a negative selection step and a positive selection step are each performed to identify candidate proteins.

According to certain aspects of the invention, a microorganism is genetically modified to include one or more exogenous nucleic acids encoding for an allosteric protein. The allosteric protein sequence can be identified based on published literature search. For example, biosynthetic pathways for the effectors and allosteric proteins are fully described in the following references: cdaR (Monterrubio et al. 2000 *J. Bacteriol.* 182(9):2672-4), tetR (Lutz and Bujard *Nucleic Acids* Res. 1997 25(6):1203-10), aikS (Canosa et al. *Mol. Micriobiol.* 2000 35(4):791-9), ttgR (Teran, et al. *Antimicrob. Agents Chemother.* 47(10):3067-72 (2003)), btuB riboswitch (Nahvi, et al. *Nucleic Acids Res.* 32:143-150 (2004)); glucaric acid (Moon, et al. *Appl. Env. Microbiol.* 75:589-595 (2009)), naringenin (Santos, et al. *Metabolic Engineering.* 13:392-400 (2011)), alkanes (Steen, et al. 463:559-562 (2009)), cobalamin (Raux, et al. *Cell Mol. Life Sci.* 57:1880-1893. (2000)), muconic acid (Niu, et al. *Biotechnol Prog.* 18:201-211. (2002)). A non-exhaustive list of sensor genes suitable for use according to certain aspects of the invention is provided at table 1. Methods described herein can be used to insert the nucleic acids into the genome of the microorganism that are responsible for production of allosteric proteins.

TABLE 1

| Sensor Gene | Molecule | Type of Sensor |
| --- | --- | --- |
| cdaR | glucaric acid | Transcriptional activator |
| ttgR | naringennin (flavonoids) | Transcriptional repressor |
| btuB riboswitch | cobalamin | Riboswitch |
| mphR | macrolides | Transcriptional repressor |
| tetR | tetracycline derivates | Transcriptional repressor |
| benM | muconic acid | Transcriptional activator |
| alkS | medium chain n-alkanes | Transcriptional activator |
| xylR | xylose | Transcriptional activator |
| araC | Arabinose | Transcriptional activator |
| gntR | Gluconate | Transcriptional repressor |
| galS | Galactose | Transcriptional repressor |
| trpR | tryptophan | Transcriptional repressor |
| qacR | Berberine | Transcriptional repressor |
| rmrR | Phytoalexin | Transcriptional repressor |

TABLE 1-continued

| Sensor Gene | Molecule | Type of Sensor |
| --- | --- | --- |
| cymR | Cumate | Transcriptional repressor |
| melR | Melibiose | Transcriptional activator |
| rafR | Raffinose | Transcriptional activator |
| nahR | Salicylate | Transcriptional activator |
| nocR | Nopaline | Transcriptional activator |
| clcR | Chlorobenzoate | Transcriptional activator |
| varR | Virginiamycin | Transcriptional repressor |
| rhaR | Rhamnose | Transcriptional repressor |
| PhoR | Phosphate | Two-component system |
| MalK | Malate | Two-component system |
| GlnK | Glutamine | Two-component system |
| Retinoic acid receptor | Retinoic acid | Nuclear hormone receptor |
| Estrogen receptor | Estrogen | Nuclear hormone receptor |
| Ecdysone receptor | Ecdysone | Nuclear hormone receptor |

In certain exemplary embodiments, methods of negatively selecting a microorganism expressing a mutant allosteric protein that does not undergo an allosteric conformational change and/or that undergoes an incorrect allosteric conformational change upon effector binding are provided. In other exemplary embodiments, methods of positively selecting a microorganism expressing a mutant allosteric protein that undergoes an allosteric conformational change and/or binds an effector molecule are provided.

According to certain aspects of the invention, a microorganism is genetically modified to include one or more exogenous nucleic acids encoding an antidote to a toxin. Antidote and toxin pairs are known to those of skill in the art and include, but are not limited to, SDS:tolC, colicin:tolC (negative selection), kanamycin: kanamycin nucleotidyl-transferase, chloramphenicol:chloramphenicol acyl tranferase, ampicillin:beta lactamase, tetracycline:tetracycline efflux pump tetA, nickel chloride: tetracycline efflux pump tetA (negative selection), 5-fluoroorotic acid: URA3 (negative selection). The transformed microorganism is intended to express the antidote under suitable conditions.

The genes for production of any particular antidote are known to those of skill in the art. For example, the genes for the above antidotes are fully described in tetA (Postle et al. *Nucleic Acid Research* 1984 12(12)4849-4863) tolC (Fralick *J. Bacteriol.* 1996 178(19)5803-5805) Chloramphenicol acetyl tranfersase (Shaw et al. *J. Bacteriol.* 1970 104(3): 1095-1105). Methods described herein can be used to insert the nucleic acids into the genome of the microorganism that are responsible for production of DNA binding proteins.

According to one aspect, the transformed, recombinant microorganism expresses the allosteric protein which regulates production of the antidote. When expressed, the allosteric protein prevents the cell from expressing the antidote gene, either by blocking the expression (i.e. a repressor) or failing to activate the expression (i.e. activator) of the antidote unless the allosteric protein is bound by the target allosteric effector, which leads to antidote expression by changing allosteric protein function. Several regulation mechanisms are possible. For an allosteric transcription factor that is a repressor, the repressor protein blocks transcription of the antidote gene by binding a region of DNA 5' to the antidote gene unless the desired allosteric effector binds the repressor. For an allosteric transcription factor that is an activator, the activator recruits RNA polymerase to a region of DNA 5' to the antidote gene only when the desired allosteric effector binds to the activator. For an attenuating allosteric protein, the allosteric protein is encoded in the 5' untranslated region of a repressor regulating the transcription of the antidote gene, and attenuates translation of this repressor when bound to the target allosteric effector. (See U.S. Ser. No. 61/781,373, filed Mar. 14, 2013, which is hereby incorporated by reference in its entirety for all purposes.)

According to another aspect, the allosteric protein includes instances where the effector binding domain and the DNA binding domain are not in the same polypeptide chain, for example, a two-component system or nuclear hormone receptors. Upon effector binding, the effector binding domain relays the signal through one or more intermediary proteins, resulting in transcription regulation at a defined locus.

According to a further aspect, the transformed, the allosteric effector, exogenously provided, binds to the allosteric protein in a manner to promote production of the antidote. According to one aspect, the production of the antidote is proportional to the amount of allosteric effector bound to the allosteric protein. In the absence of the allosteric effector, the allosteric protein prevents production of antidote.

In certain aspects of the invention, one or more allosteric proteins are used to control expression of one or more detectable markers in a microorganism. In certain aspects, one or more detectable markers are used in conjunction with toxin selection. In other aspects, one or more detectable markers are used as a stand-alone detection technique. In certain aspects, an allosteric protein and/or allosteric effector controls the expression of a marker (e.g., a detectable marker) or of a moiety (e.g., an amino acid sequence or a nucleic acid sequence) that can detectably labeled.

Examples of detectable markers include various radioactive moieties, enzymes, prosthetic groups, fluorescent markers, luminescent markers, bioluminescent markers, metal particles, protein-protein binding pairs, protein-antibody binding pairs and the like. Detectable markers are commercially available from a variety of sources.

In certain aspects of the invention, detectable proteins and/or protein tags are provided. Examples of detectable fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of detectable bioluminescent proteins include, but are not limited to, luciferase (e.g., bacterial, firefly, click beetle and the like), luciferin, aequorin and the like. Examples of detectable enzyme systems include, but are not limited to, galactosidases, glucorinidases, phosphatases, peroxidases, cholinesterases and the like.

Biotin, or a derivative thereof, may also be used as a detectable label, and subsequently bound by a detectably labeled avidin/streptavidin derivative (e.g. phycoerythrin-conjugated streptavidin), or a detectably labeled anti-biotin antibody. Digoxigenin may be expressed subsequently bound by a detectably labeled anti-digoxigenin antibody (e.g. fluoresceinated anti-digoxigenin). In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for detection include one or more protein tags. As used herein, the term "protein tag" refers to a heterologous polypeptide sequence linked to a polymerase of the invention. Protein tags include, but are not limited to, Avi tag (GLNDIFEAQKIEWHE) (SEQ ID NO:1), calmodulin tag (KRRWKKNFIAVSAANRFKKISSSGAL) (SEQ ID NO:2), FLAG tag (DYKDDDDK) (SEQ ID NO:3), HA tag (YPYDVPDYA) (SEQ ID NO:4), His tag (HHHHHH) (SEQ ID NO:5), Myc tag (EQKLISEEDL) (SEQ ID NO:6), S tag (KETAAAKFERQHMDS) (SEQ ID NO:7), SBP tag (MDEKTTGWRGGHVVEGLAGELEQLRARLEHH-PQGQREP) (SEQ ID NO:8), Softag 1 (SLAELL-NAGLGGS) (SEQ ID NO:9), Softag 3 (TQDPSRVG) (SEQ ID NO:17), V5 tag (GKPIPNPLLGLDST) (SEQ ID NO:10), Xpress tag (DLYDDDDK) (SEQ ID NO:11), Iso-peptag (TDKDMTITFTNKKDAE) (SEQ ID NO:12), Spy-Tag (AHIVMVDAYKPTK) (SEQ ID NO:13), streptactin tag (Strep-tag II: WSHPQFEK) (SEQ ID NO:14) and the like.

Detection method(s) used will depend on the particular detectable labels used in the microorganism. In certain exemplary embodiments, microorganisms may be selected for and/or screened for using a microscope, a spectrophotometer, a tube luminometer or plate luminometer, x-ray film, magnetic fields, a scintillator, a fluorescence activated cell sorting (FACS) apparatus, a microfluidics apparatus, a bead-based apparatus or the like.

In certain exemplary embodiments, one or more nucleic acid sequences encoding the candidate protein sequences are expressed in a host cell using standard techniques of molecular biology. Standard recombinant DNA and molecular cloning techniques used herein are well known in the art and are described in Sambrook, J., Fritsch, E. F. and Maniatis, T., *Molecular Cloning: A Laboratory Manual*, 2$^{nd}$ ed.; Cold Spring Harbor Laboratory: Cold Spring Harbor, N.Y., (1989) and by Silhavy, T. J., Bennan, M. L. and Enquist, L. W., *Experiments with Gene Fusions*; Cold Spring Harbor Laboratory: Cold Spring Harbor, N.Y., (1984); and by Ausubel, F. M. et al., *Current Protocols in Molecular Biology*, Greene Publishing and Wiley-Interscience (1987) each of which are hereby incorporated by reference in their entireties. Additional useful methods are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992) each of which are hereby incorporated by reference in their entireties.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

As used herein, the term "amino acid" includes organic compounds containing both a basic amino group and an acidic carboxyl group. Included within this term are natural amino acids (e.g., L-amino acids), modified and unusual amino acids (e.g., D-amino acids and -amino acids), as well as amino acids which are known to occur biologically in free or combined form but usually do not occur in proteins. Natural protein occurring amino acids include alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,- triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, .alpha.-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, the term "peptide" includes compounds that consist of two or more amino acids that are linked by means of a peptide bond. Peptides may have a molecular weight of less than 10,000 Daltons, less than 5,000 Daltons, or less than 2,500 Daltons. The term "peptide" also includes compounds containing both peptide and non-peptide components, such as pseudopeptide or peptidomimetic residues or other non-amino acid components. Such compounds containing both peptide and non-peptide components may also be referred to as a "peptide analog."

As used herein, the term "protein" includes compounds that consist of amino acids arranged in a linear chain and joined together by peptide bonds between the carboxyl and amino groups of adjacent amino acid residues.

Microorganisms may be genetically modified to delete genes or incorporate genes by methods known to those of skill in the art. Vectors and plasmids useful for transformation of a variety of host cells are common and commercially available from companies such as Invitrogen Corp. (Carlsbad, Calif.), Stratagene (La Jolla, Calif.), New England Biolabs, Inc. (Beverly, Mass.) and Addgene (Cambridge, Mass.).

Certain aspects of the invention pertain to vectors, such as, for example, expression vectors. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, an exogenous nucleic acid described herein is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy on can be included such that a higher copy number can be obtained (e.g., pCC1FOS™, pCC2FOS™). Fosmid libraries are particularly useful for constructing stable libraries from complex genomes. Fosmids and fosmid library production kits are commercially available (EPICENTRE® Biotechnologies, Madison, Wis.). For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). It will be appreciated by those skilled in the art that the design of the expression vector can depend on such factors as the choice of the host cell to be transformed, the level of expression of protein desired, and the like.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells, a virion, a virosome, a virus-like particle, a parasitic microbe, an infectious protein and the like. Cells include eukaryotic cells such as yeast cells, plant cells, and animal cells. Particular cells include bacterial cells. Other suitable cells are known to those skilled in the art.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression in gram positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in gram negative bacteria (Scott et al., Plasmid 50(1):74-79 (2003)). Several plasmid derivatives of broad-host-range Inc P4 plasmid RSF1010 are also available with promoters that can function in a range of gram negative bacteria. Plasmid pAYC36 and pAYC37, have active promoters along with multiple cloning sites to allow for the heterologous gene expression in gram negative bacteria.

Chromosomal gene replacement tools are also widely available. For example, a thermosensitive variant of the broad-host-range replicon pWV101 has been modified to construct a plasmid pVE6002 which can be used to create gene replacement in a range of gram positive bacteria (Maguin et al., J. Bacteriol. 174(17):5633-5638 (1992)). Additionally, in vitro transposomes are available to create random mutations in a variety of genomes from commercial sources such as EPICENTRE® (Madison, Wis.).

Vectors useful for the transformation of *E. coli* are common and commercially available. For example, the desired genes may be isolated from various sources, cloned onto a modified pUC19 vector and transformed into *E. coli* host cells. Alternatively, the genes encoding a desired biosynthetic pathway may be divided into multiple operons, cloned into expression vectors, and transformed into various *E. coli* strains.

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAM 1 and derivatives thereof (Renault et al., Gene 183:175-182 (1996); and O'Sullivan et al., Gene 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg R, Golic N, Bongers R, Leer R J, de Vos W M, Siezen R J, Kleerebezem M. Appl. Environ. Microbiol. 2005 March; 71(3): 1223-1230), which may be used for transformation.

Initiation control regions or promoters, which are useful to drive expression of the relevant pathway coding regions in the desired *Lactobacillus* host cell, may be obtained from *Lactobacillus* or other lactic acid bacteria, or other gram positive organisms. A non-limiting example is the nisA promoter from *Lactococcus*. Termination control regions may also be derived from various genes native to the preferred hosts or related bacteria.

The various genes for a desired biosynthetic or other desired pathway may be assembled into any suitable vector, such as those described above. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (*Molecular Genetics and Genomics* 224:1252-154 (1990)), Bringel and Hubert (*Appl. Microbiol. Biotechnol.* 33: 664-670 (1990)), and Teresa Alegre, Rodriguez and Mesas (*FEMS Microbiology Letters* 241:73-77 (2004)). Plasmids can also be introduced to *Lactobacillus plantatrum* by conjugation (Shrago, Chassy and Dobrogosz *Appl. Environ. Micro.* 52: 574-576 (1986)). The desired biosynthetic pathway genes can also be integrated into the chromosome of *Lactobacillus* using integration vectors (Hols et al. *Appl. Environ. Micro.* 60:1401-1403 (1990); Jang et al. Micro. Lett. 24:191-195 (2003)).

Microorganisms which may serve as host cells and which may be genetically modified to produce recombinant microorganisms as described herein include, but are not limited to, gram positive bacteria, gram negative bacteria, acid-fast bacteria and the like.

As used herein, gram positive bacteria include, but are not limited to, *Actinomedurae, Actinomyces israelii, Bacillus anthracia, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like.

As used herein, gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like.

As used herein, acid-fast bacteria include, but are not limited to, *Myobacterium avium, Myobacterium leprae, Myobacterium* tuberculosis and the like.

As used herein, other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium*, Meningococci and the like.

In certain aspects, microorganisms which may serve as host cells and which may be genetically modified to produce recombinant microorganisms as described herein include, but are not limited to, genera *Clostridium, Escherichia, Rhodococcus, Pseudomonas, Bacillus, Lactobacillus Saccharomyces,* and *Enterococcus*. Particularly suitable microorganisms include *Escherichia coli, Bacillus subtilis* and *Saccharomyces cerevisiae*.

According to certain aspect of the invention, phages and their genetic material are provided. As used herein, the terms "phage" and "bacteriophage" are used interchangeably. Phage can be distinguished from each another based on their genetic composition and/or their virion morphology. Some phage have double stranded DNA genomes, including phage of the corticoviridae, lipothrixviridae, plasmaviridae, myrovridae, siphoviridae, *sulfolobus shibate*,podoviridae, tectiviridae and fuselloviridae families. Other phage have single stranded DNA genomes, including phage of the microviridae and inoviridae families. Other phage have RNA genomes, including phage of the leviviridae and Cystoviridae families. Exemplary bacteriophage include, but are not limited to, Wphi, Mu, T1, T2, T3, T4, T5, T6, T7, P1, P2, P4, P22, fd, phi6, phi29, phiC31, phi80, phiX174, SP01, M13, MS2, PM2, SSV-1, L5, PRD1, Qbeta, lambda, UC-1, HK97, HK022 and the like.

According to certain exemplary embodiments, microarrays are provided having nucleic acids attached thereto encoding one or a plurality of the allosteric proteins described herein. As used herein, "microarray" refers in one embodiment to a type of multiplex assay product that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable. Probes immobilized on microarrays include nucleic acids, such as oligonucleotide barcodes, that are generated in or from an assay reaction. Typically, the oligonucleotides or polynucleotides on microarrays are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics* Supplement, 21:1-60 (1999); and Fodor et al., U.S. Pat. Nos. 5,424,186; 5,445,934; and 5,744,305. A microarray may comprise arrays of microbeads, or other microparticles, alone or disposed on a planar surface or in wells or other physical configurations that can be sued to separate the beads. Such microarrays may be formed in a variety of ways, as disclosed in the following exemplary references: Brenner et al. (2000) *Nat. Biotechnol.* 18:630; Tulley et al., U.S. Pat. No. 6,133,043; Stuelpnagel et al., U.S. Pat. No. 6,396,995; Chee et al., U.S. Pat. No. 6,544,732; and the like. In one format, microarrays are formed by randomly disposing microbeads having attached oligonucleotides on a surface followed by determination of which microbead carries which oligonucleotide by a decoding procedure, e.g. as disclosed by Gunderson et al., U.S. Patent Pub. No. 2003/0096239.

"Microarrays" or "arrays" can also refer to a heterogeneous pool of nucleic acid molecules that is distributed over a support matrix. The nucleic acids can be covalently or non-covalently attached to the support. Preferably, the nucleic acid molecules are spaced at a distance from one another sufficient to permit the identification of discrete features of the array. Nucleic acids on the array may be non-overlapping or partially overlapping. Methods of transferring a nucleic acid pool to support media is described in U.S. Pat. No. 6,432,360. Bead based methods useful for the methods described herein are disclosed in PCT US05/04373.

"Amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

"Support" can refer to a matrix upon which nucleic acid molecules of a nucleic acid array are placed. The support can be solid or semi-solid or a gel. "Semi-solid" refers to a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

"Randomly-patterned" or "random" refers to non-ordered, non-Cartesian distribution (in other words, not arranged at pre-determined points along the x- or y-axes of a grid or at defined "clock positions," degrees or radii from the center of a radial pattern) of nucleic acid molecules over a support, that is not achieved through an intentional design (or program by which such design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon. Arrays of the invention can be randomly patterned or random.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

In certain aspects of the invention, methods and compositions for "stitching" one or more nucleic acid sequences together to encode an allosteric protein are provided. As used herein, the term "stitching" refers to the linking of a plurality of nucleic acid sequences, for example, via an amplification reaction such as barcode crossover PCR, or an extension reaction.

In certain aspects, methods of amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683, 202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391, 544, 6,365,375, 6,294,323, 6,261,797, 6,124,090 and 5,612, 199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art. polymerase and/or ligase chain reactions. thermal cycling (PCR) or isothermally (e.g. RCA, hRCA, SDA, HDA, PWGA (Worldwide Website: biohelix.com/technology.asp)).

PCR refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research,* 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.,* 273:221-228 (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Techniques for quantitative PCR are well-known to those of ordinary skill in the art, as exemplified in the following references: Freeman et al., *Biotechniques,* 26:112-126 (1999); Becker-Andre et al., *Nucleic Acids Research,* 17:9437-9447 (1989); Zimmerman et al., *Biotechniques,* 21:268-279 (1996); Diviacco et al., *Gene,* 122:3013-3020 (1992); Becker-Andre et al., *Nucleic Acids Research,* 17:9437-9446 (1989); and the like.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figure and accompanying claims.

EXAMPLE I

Computational Protein Design

In certain embodiments of the invention, structure-based protein design is combined with state-of-the-art software (e.g., Rosetta software) to design small molecule-protein interactions. The binding pocket of an allosteric protein is designed to target a small molecule. Thousands of in silico filtered protein designs are generated that can potentially bind to small molecules.

EXAMPLE II

Chip-based DNA Synthesis and Assembly of Designs

In certain embodiments, the allosteric proteins designed in Example I are encoded by DNA immobilized on a substrate (e.g., on DNA chips). In certain aspects, multiple small molecule targets (e.g., small molecule-binding proteins, e.g., allosteric proteins) are encoded on a single chip. For a given allosteric protein, the corresponding DNA sequences encoding the protein are selectively amplified and purified. In certain aspects, each DNA sequence on the chip is approximately 100 bases long. Amplified DNA sequences are stitched to assemble a sequence encoding an allosteric protein. A hierarchical assembly technique was developed to build full design libraries encoding multiple allosteric proteins. Methods of hierarchical assembly are described in U.S. Ser. No. 12/533,141, filed Jul. 31, 2009, incorporated herein by reference in its entirety for all purposes.

Assembly

Designs arising from computational binding predictions or other methods are assembled using a multiplexed assembly strategy. Library fragments are amplified from oligos generated, e.g., by printing on a microchip, standard capillary synthesis, from the wild-type sequence, or from previous library versions. Amplification sequences are removed, for example, by type IIs restriction endonucleases. Fragments are assembled into sub-gene fragments or full genes in a multiplexed reaction using ligase or other means. Sub-gene fragments are assembled into full-length designs and combinations thereof in multiplex, using, e.g., overlap PCR, ligation, or other suitable methods known to those of skill in the art. Full genes are inserted into an expression plasmid e.g., by ligation, Gibson assembly or other suitable methods known to those of skill in the art in a multiplex reaction. Expression plasmid libraries are transformed into a strain that allows high cloning efficiency, or directly into a strain competent for binding and/or activation sites of sensor proteins. Functional sensor proteins are identified using selection, screening or a combination thereof.

EXAMPLE III

Genetic Selection System

A novel genetic selection system to identify the best allosteric protein designs was developed. Typical selection systems known to others in the art at the time of filing optimize a single desired function. In contrast, embodiments of the present invention optimize two functions: 1) binding affinity of the target small molecule for the allosteric protein; and 2) preserving allostery in the allosteric protein. In certain aspects, the selection system of the invention utilizes a dual selective marker, which is optionally activated in two stages. In the first selection step, designed proteins that are not allosteric are eliminated by negative selection. In the second selection step, designed proteins that were not eliminated in the first selection stage are evaluated for binding a target small molecule by positive selection. The selection system of the present invention allows for evaluating nearly a billion protein designs. Protein designs that survive both selection stages are individually assayed for activity.

What is claimed:

1. A method of making and isolating allosteric DNA binding proteins that bind to a companion allosteric effector that induces a conformation change comprising:

computationally designing in silico candidate allosteric DNA binding proteins having a binding pocket for a companion allosteric effector, providing nucleic acid sequences encoding the candidate allosteric DNA binding proteins, introducing the nucleic acid sequences into bacterial host cells and expressing the candidate allosteric DNA binding proteins, determining whether the candidate allosteric DNA binding proteins bind to DNA and inhibit expression of a gene by using negative selection to identify a first plurality of bacterial host cells where the candidate allosteric DNA binding proteins have bound to DNA and inhibit expression of the gene, and determining whether the candidate allosteric DNA binding proteins in the first plurality of bacterial host cells bind to the companion allosteric effector using positive selection to identify a second plurality of bacterial host cells where the candidate allosteric DNA binding proteins have bound to the companion allosteric effector.

2. The method of claim 1, wherein nucleic acid sequences encoding the candidate allosteric DNA binding proteins are created from nucleic acid subsequences bound to a substrate.

3. The method of claim 2, wherein a plurality of subsequences from the substrate are ligated to form the nucleic acid sequences encoding the candidate allosteric DNA binding proteins.

4. The method of claim 1, wherein the negative selection includes contacting the bacterial host cells with a toxin that is toxic to cells which express the gene.

5. The method of claim 1, wherein the negative selection includes contacting the bacterial host cells with a toxin that is toxic to cells where the candidate allosteric DNA binding proteins have not bound to DNA to inhibit expression of the gene.

6. The method of claim 1, wherein the positive selection includes contacting the first plurality of bacterial host cells with a toxin and the companion allosteric effector, wherein the toxin is toxic to cells where the gene is not expressed.

7. The method of claim 1, wherein the positive selection includes contacting the first plurality of bacterial host cells with a toxin and allosteric effector targets, wherein the toxin is toxic to cells where the companion allosteric effector has not bound to the candidate allosteric DNA binding proteins in a manner to release the candidate allosteric DNA binding proteins from the DNA.

8. The method of claim 1, wherein the positive selection includes detecting a detectable marker that is expressed in the first plurality of bacterial cells when the candidate allosteric DNA binding proteins have bound to the DNA to express the gene.

9. The method of claim 8, wherein the detectable marker is a fluorescent protein.

10. The method of claim 9, wherein the fluorescent protein is detected by fluorescence activated cell sorting.

11. The method of claim 7, wherein the positive selection further comprises detecting a detectable marker that is expressed in the first plurality of bacterial cells when the companion allosteric effector has not bound to the candidate allosteric DNA binding proteins in a manner to release the candidate allosteric DNA binding proteins from the DNA.

12. The method of claim 1, wherein the DNA binding proteins are chemical sensors.

13. The method of claim 1, wherein the bacterial host cells are *Escherichia coli* or *Bacillus subtilis*.

14. A method of making and isolating allosteric DNA binding proteins that bind to a companion allosteric effector that induces a conformation change comprising:
computationally designing in silico candidate allosteric DNA binding proteins having a binding pocket for a companion allosteric effector,
providing nucleic acid sequences encoding the candidate allosteric DNA binding proteins, introducing the nucleic acid sequences into *Saccharomyces cerevisiae* host cells and expressing the candidate allosteric DNA binding proteins,
determining whether the candidate allosteric DNA binding proteins bind to DNA and inhibit expression of a gene by using negative selection to identify a first plurality of *Saccharomyces cerevisiae* host cells where the candidate allosteric DNA binding proteins have bound to DNA and inhibit expression of the gene, and
determining whether the candidate allosteric DNA binding proteins in the first plurality of *Saccharomyces cerevisiae* host cells bind to the companion allosteric effector using positive selection to identify a second plurality of *Saccharomyces cerevisiae* host cells where the candidate allosteric DNA binding proteins have bound to the companion allosteric effector.

15. The method of claim 14, wherein nucleic acid sequences encoding the candidate allosteric DNA binding proteins are created from nucleic acid subsequences bound to a substrate, and are ligated to form the nucleic acid sequences encoding the candidate allosteric DNA binding proteins.

16. The method of claim 14, wherein the negative selection includes contacting the bacterial host cells with a toxin that is toxic to cells which express the gene.

17. The method of claim 14, wherein the positive selection includes contacting the first plurality of bacterial host cells with a toxin and the companion allosteric effector, wherein the toxin is toxic to cells where the gene is not expressed.

18. A method of making and isolating allosteric DNA binding proteins that bind to a companion allosteric effector that induces a conformation change comprising:
computationally designing in silico candidate allosteric DNA binding proteins having a binding pocket for a companion allosteric effector,
providing nucleic acid sequences encoding the candidate allosteric DNA binding proteins created from nucleic acid subsequences bound to a substrate,
introducing the nucleic acid sequences into microorganisms and expressing the candidate allosteric DNA binding proteins,
determining whether the candidate allosteric DNA binding proteins bind to DNA and inhibit expression of a gene by using negative selection to identify a first plurality of microorganisms where the candidate allosteric DNA binding proteins have bound to DNA and inhibit expression of the gene, and
determining whether the candidate allosteric DNA binding proteins in the first plurality of microorganisms bind to the companion allosteric effector using positive selection to identify a second plurality of microorganisms where the candidate allosteric DNA binding proteins have bound to the companion allosteric effector.

19. The method of claim 18, wherein the substrate is a microarray.

20. The method of claim 19, wherein a plurality of subsequences from the substrate are amplified from sequences on the microarray and ligated to form the nucleic acid sequences encoding the candidate allosteric DNA binding proteins.

21. The method of claim 18, wherein the nucleic acid sequences encoding the candidate allosteric DNA binding proteins are generated randomly.

22. The method of claim 21, wherein the candidate allosteric DNA binding proteins are generated by error-prone PCR or combinatorial PCR.

23. The method of claim 18, wherein the candidate allosteric DNA binding proteins are fused to an anti-toxin gene requiring the protein reading frame to remain intact for its function.

24. The method of claim 23, wherein a candidate allosteric DNA binding protein that is out of frame or truncated does not allow expression of an anti-toxin protein specific against a toxin.

25. The method of claim 24, wherein a host cell expressing an out of frame or truncated candidate allosteric DNA binding protein is eliminated by exposing the host cell to the toxin.

26. A cell including a nucleic acid sequence encoding for a computationally in silico designed allosteric DNA binding protein having a binding pocket for an effector molecule and a nucleic acid sequence encoding for the effector molecule having a structure that selectively binds to the binding pocket of the computationally in silico designed allosteric DNA binding protein.

27. The cell of claim 26 further including an exogenous gene which is regulated by the allosteric DNA binding protein.

28. The cell of claim 26 further including an exogenous gene which is regulated by the allosteric DNA binding protein and the effector molecule.

29. The cell of claim 26 wherein the exogenous gene encodes an antidote for a toxin.

30. The cell of claim 26 wherein the exogenous gene encodes for a detectable protein or detectable protein tag.

31. The cell of claim 26 wherein the allosteric DNA binding protein is fused to an antidote gene and having an intact protein reading frame.

* * * * *

SEQUENCE LISTING

```
<160> NUMBER OF SEQ ID NOS: 17

<210> SEQ ID NO 1
<211> LENGTH: 15
<212> TYPE: PRT
<213> ORGANISM: Artificial
<220> FEATURE:
<223> OTHER INFORMATION: Avi tag

<400> SEQUENCE: 1

Gly Leu Asn Asp Ile Phe Glu Ala Gln Lys Ile Glu Trp His Glu
1               5                   10                  15

<210> SEQ ID NO 2
<211> LENGTH: 26
<212> TYPE: PRT
<213> ORGANISM: Artificial
```

```
<220> FEATURE:
<223> OTHER INFORMATION: calmodulin tag

<400> SEQUENCE: 2

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 3
<211> LENGTH: 8
<212> TYPE: PRT
<213> ORGANISM: Artificial
<220> FEATURE:
<223> OTHER INFORMATION: FLAG tag

<400> SEQUENCE: 3

Asp Tyr Lys Asp Asp Asp Asp Lys
1               5

<210> SEQ ID NO 4
<211> LENGTH: 9
<212> TYPE: PRT
<213> ORGANISM: Artificial
<220> FEATURE:
<223> OTHER INFORMATION: HA tag

<400> SEQUENCE: 4

Tyr Pro Tyr Asp Val Pro Asp Tyr Ala
1               5

<210> SEQ ID NO 5
<211> LENGTH: 6
<212> TYPE: PRT
<213> ORGANISM: Artificial
<220> FEATURE:
<223> OTHER INFORMATION: His tag

<400> SEQUENCE: 5

His His His His His His
1               5

<210> SEQ ID NO 6
<211> LENGTH: 10
<212> TYPE: PRT
<213> ORGANISM: Artificial
<220> FEATURE:
<223> OTHER INFORMATION: Myc tag

<400> SEQUENCE: 6

Glu Gln Lys Leu Ile Ser Glu Glu Asp Leu
1               5                   10

<210> SEQ ID NO 7
<211> LENGTH: 15
<212> TYPE: PRT
<213> ORGANISM: Artificial
<220> FEATURE:
<223> OTHER INFORMATION: S tag

<400> SEQUENCE: 7

Lys Glu Thr Ala Ala Ala Lys Phe Glu Arg Gln His Met Asp Ser
1               5                   10                  15
```

```
<210> SEQ ID NO 8
<211> LENGTH: 38
<212> TYPE: PRT
<213> ORGANISM: Artificial
<220> FEATURE:
<223> OTHER INFORMATION: SBP tag

<400> SEQUENCE: 8

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 9
<211> LENGTH: 13
<212> TYPE: PRT
<213> ORGANISM: Artificial
<220> FEATURE:
<223> OTHER INFORMATION: Softtag 1

<400> SEQUENCE: 9

Ser Leu Ala Glu Leu Leu Asn Ala Gly Leu Gly Gly Ser
1               5                   10

<210> SEQ ID NO 10
<211> LENGTH: 14
<212> TYPE: PRT
<213> ORGANISM: Artificial
<220> FEATURE:
<223> OTHER INFORMATION: V5 tag

<400> SEQUENCE: 10

Gly Lys Pro Ile Pro Asn Pro Leu Leu Gly Leu Asp Ser Thr
1               5                   10

<210> SEQ ID NO 11
<211> LENGTH: 8
<212> TYPE: PRT
<213> ORGANISM: Artificial
<220> FEATURE:
<223> OTHER INFORMATION: Xpress tag

<400> SEQUENCE: 11

Asp Leu Tyr Asp Asp Asp Asp Lys
1               5

<210> SEQ ID NO 12
<211> LENGTH: 16
<212> TYPE: PRT
<213> ORGANISM: Artificial
<220> FEATURE:
<223> OTHER INFORMATION: Isopeptag

<400> SEQUENCE: 12

Thr Asp Lys Asp Met Thr Ile Thr Phe Thr Asn Lys Lys Asp Ala Glu
1               5                   10                  15

<210> SEQ ID NO 13
<211> LENGTH: 13
<212> TYPE: PRT
<213> ORGANISM: Artificial
<220> FEATURE:
<223> OTHER INFORMATION: SpyTag
```

```
<400> SEQUENCE: 13

Ala His Ile Val Met Val Asp Ala Tyr Lys Pro Thr Lys
1               5                   10

<210> SEQ ID NO 14
<211> LENGTH: 8
<212> TYPE: PRT
<213> ORGANISM: Artificial
<220> FEATURE:
<223> OTHER INFORMATION: streptactin tag

<400> SEQUENCE: 14

Trp Ser His Pro Gln Phe Glu Lys
1               5

<210> SEQ ID NO 15

<400> SEQUENCE: 15

000

<210> SEQ ID NO 16

<400> SEQUENCE: 16

000

<210> SEQ ID NO 17
<211> LENGTH: 8
<212> TYPE: PRT
<213> ORGANISM: Artificial
<220> FEATURE:
<223> OTHER INFORMATION: Softtag 3

<400> SEQUENCE: 17

Thr Gln Asp Pro Ser Arg Val Gly
1               5
```